US008975024B2

(12) United States Patent
Macevicz

(10) Patent No.: US 8,975,024 B2
(45) Date of Patent: *Mar. 10, 2015

(54) METHODS FOR SEQUENCING POLYNUCLEOTIDES

(71) Applicant: Illumina, Inc., San Diego, CA (US)

(72) Inventor: Stephen C. Macevicz, Cupertino, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/044,413

(22) Filed: Oct. 2, 2013

(65) Prior Publication Data

US 2014/0057274 A1    Feb. 27, 2014

Related U.S. Application Data

(60) Continuation of application No. 13/622,273, filed on Sep. 18, 2012, now Pat. No. 8,557,521, which is a continuation of application No. 12/558,396, filed on Sep. 11, 2009, now Pat. No. 8,288,095, which is a continuation of application No. 10/962,337, filed on Oct. 8, 2004, now Pat. No. 7,598,035, which is a division of application No. 10/706,118, filed on Nov. 12, 2003, now abandoned, which is a division of application No. 09/549,748, filed on Apr. 14, 2000, now Pat. No. 6,720,179, which is a division of application No. 09/028,128, filed on Feb. 23, 1998, now Pat. No. 6,054,276.

(51) Int. Cl.
| | |
|---|---|
| *C12Q 1/68* | (2006.01) |
| *C12P 19/34* | (2006.01) |
| *C07H 21/02* | (2006.01) |
| *C07H 21/04* | (2006.01) |
| *C12N 15/10* | (2006.01) |
| *C12N 15/64* | (2006.01) |
| *C12N 15/66* | (2006.01) |
| *G06F 19/22* | (2011.01) |

(52) U.S. Cl.
CPC .............. *C12Q 1/6869* (2013.01); *C12N 15/10* (2013.01); *C12N 15/64* (2013.01); *C12N 15/66* (2013.01); *C12Q 1/6809* (2013.01); *C12Q 1/683* (2013.01); *C12Q 1/6841* (2013.01); *C12Q 1/6872* (2013.01); *C12Q 1/6874* (2013.01); *G06F 19/22* (2013.01)
USPC .......... 435/6.1; 435/6.11; 435/6.12; 435/91.1; 435/91.2; 536/23.1; 536/24.3; 536/24.33

(58) Field of Classification Search
CPC .... C12Q 1/6813; C12Q 1/6816; C12Q 1/682; C12Q 1/6841; C12Q 1/6844; C12Q 1/6846; C12Q 1/6851; C12Q 1/6858; C12Q 1/6862; C12Q 1/6865

USPC .......... 435/6.1, 6.11, 6.12, 91.1, 91.2, 91.51; 436/94, 501; 536/23.1, 24.3, 24.33, 536/25.3
See application file for complete search history.

(56) References Cited

U.S. PATENT DOCUMENTS

| | | | |
|---|---|---|---|
| 4,293,652 A | 10/1981 | Cohen | |
| 5,102,785 A | 4/1992 | Livak et al. | |
| 5,194,596 A | 3/1993 | Tischer et al. | |
| 5,196,328 A | 3/1993 | Tartof | |
| 5,367,065 A * | 11/1994 | Ecker et al. ................. | 536/23.6 |
| 5,409,897 A | 4/1995 | Thomas et al. | |
| 5,508,169 A | 4/1996 | Deugau et al. | |
| 5,512,478 A * | 4/1996 | Orser et al. ............... | 435/252.33 |
| 5,523,221 A | 6/1996 | Weiner | |
| 5,604,097 A | 2/1997 | Brenner | |
| 5,658,736 A | 8/1997 | Wong | |
| 5,667,970 A | 9/1997 | Zhang | |
| 5,677,153 A | 10/1997 | Botstein et al. | |
| 5,695,937 A | 12/1997 | Kinzler et al. | |
| 5,710,000 A | 1/1998 | Sapolsky et al. | |
| 5,728,524 A | 3/1998 | Sibson | |
| 5,804,382 A | 9/1998 | Sytkowski et al. | |
| 5,827,704 A | 10/1998 | Cease et al. | |
| 5,834,201 A | 11/1998 | Hartley | |
| 5,846,719 A | 12/1998 | Brenner et al. | |
| 5,861,252 A | 1/1999 | Kambara et al. | |

(Continued)

FOREIGN PATENT DOCUMENTS

| | | |
|---|---|---|
| EP | 0 593 095 | 4/1994 |
| EP | 0 761 822 | 3/1997 |

(Continued)

OTHER PUBLICATIONS

Chen et al., "Ordered shotgun sequencing, a strategy for integrated mapping and sequencing of YAC clones," Genomics, 17:651-656 (1993).

(Continued)

*Primary Examiner* — Frank Lu
(74) *Attorney, Agent, or Firm* — Knobbe Martens Olson & Bear LLP

(57) ABSTRACT

The invention relates to methods and systems for sequencing and constructing a high resolution physical map of a polynucleotide. In accordance with the invention, nucleotide sequences are determined at the ends of restriction fragments produced by a plurality of digestions with a plurality of combinations of restriction endonucleases so that a pair of nucleotide sequences is obtained for each restriction fragment. A physical map of the polynucleotide is constructed by ordering the pairs of sequences by matching the identical sequences among the pairs.

17 Claims, 4 Drawing Sheets

(56) References Cited

U.S. PATENT DOCUMENTS

| | | | |
|---|---|---|---|
| 5,939,265 | A | 8/1999 | Cohen et al. |
| 5,968,784 | A | 10/1999 | Spinella et al. |
| 6,054,276 | A | 4/2000 | Macevicz |
| 6,136,537 | A | 10/2000 | Macevicz |
| 7,598,035 | B2 | 10/2009 | Macevicz |
| 8,288,095 | B2 * | 10/2012 | Macevicz ............... 435/6.1 |
| 8,557,521 | B2 * | 10/2013 | Macevicz ............... 435/6.1 |

FOREIGN PATENT DOCUMENTS

| | | |
|---|---|---|
| WO | WO96/17082 | 6/1996 |
| WO | WO98/10095 | 3/1998 |
| WO | WO98/31838 | 7/1998 |

OTHER PUBLICATIONS

Evans, "Combinatoric strategies for genome mapping," BioEssays, 13:39-44 (1991).
Green et al., "Systematic generation of sequence-tagged sites for physical mapping of human chromosomes: application to the mapping of human chromosome 7 using yeast artificial chromosomes," Genomics, 11:548-564 (1991).
Hasan et al., "A novel multistep method for generating precise unidirectional deletions using Bsp MI, a class-IIS restriction enzyme," Gene, 50:55-62 (1986).
Hasan et al., "An Mbo II/Fok I trimming plasmid allowing consecutive cycles of precise 1- to 12-base-pair deletions in cloned DNA," Gene, 82:305-311 (1989).
Howard et al., Biotechniques, 7:940-942 (1989).
Hudson et al., "An STS-based map of the human genome," Science, 270:1945-1954 (1995).
Kato, "Description of the entire mRNA population by a 3' end cDNA fragment generated by class IIs restriction enzymes," Nucleic Acids Research, 23:3685-3690 (1995).
Kato, "RNA fingerprinting by molecular indexing," Nucleic Acids Research, 24:394-395 (1996).
Michiels et al., "Molecular approaches to genome analysis: a strategy for the construction of ordered overlapping clone libraries," CABIOS, 3: 203-210 (1987).
New England Biolabs 96/97 Catalog, p. 115. Published by New England Biolabs. Inc., 32 Tozer Road, Beverly, MA 01915-5599.
New England Biolabs 96/97 Catalog, pp. 15, 18, 22, 23 and 35. Published by New England Biolabs. Inc., 32 Tozer Road, Beverly, MA 01915-5599.
New England Biolabs 96/97 Catalog, pp. 19, 37, 108 and 109. Published by New England Biolabs. Inc., 32 Tozer Road, Beverly, MA 01915-5599.
New England Biolabs 96/97 Catalog, pp. 36 and 50. Published by New England Biolabs. Inc., 32 Tozer Road, Beverly, MA 01915-5599.
Olson et al., "Random-clone strategy for genomic restriction mapping in yeast," Proc.-Natl. Acad. Sci., 83:7826-7830 (1986).
Poustka and Lehrach, "Chromosome jumping: a long range cloning technique," in Genetic Engineering: Principles and Methods, J.K. Setlow, Editor, 10:169-193 (1988).
Poustka and Lehrach, "Jumping libraries and linking libraries: the next generation of molecular tools in mammalian genetics," Trends in Genetics, 2:174-179 (1986).
Roach et al., "Pairwise end sequencing: A unified approach to genomic mapping and sequencing," Genomics, 26:345-353 (1995).
Sapolsky et al., "Mapping genomic library clones using oligonucleotide arrays," Genomics, 33:445-456 (1996).
Smith et al., "A simple method for DNA restriction site mapping," Nucleic Acids Research, 3: 2387-2398 (1976).
Smith et al., "Genomic sequence sampling: a strategy for high resolution sequence-based physical mapping of complex genomes," Nature Genetics, 7:40-47 (1994).
Velculescu et al., "Serial analysis of gene expression," Science, 270:484-487 (1995).
Wong et al., "Multiple-complete-digest restriction fragment mapping: Generating sequence-ready maps for large-scale DNA sequencing," Proc. Natl. Acad. Sci., 94:5225-5230 (1997).
Yi et al., "Construction of restriction fragment maps of 50- to 100- kilobase DNA", Methods in Enzymology, 218:651-671 (1993).
Cease, et al., "A Vector for Facile PCR Product Cloning and Modification Generating Any Desired 4- Base 5' Overhang: pRPM" BioTechniques (1993) 14(2): 250-255.
Dobrynin, et al., "Plasmid Vectors pBBv for Cloning and Regeneration of DNA Fragments with Any End Nucleotide Sequence" Reports of the USSR Academy of Sciences (1984) 278(4): 1002-1006.
Kuznedelov, et al., "Plasmid Vector pSSCI for Cloning Synthetic Polynucleotides and Their Regeneration with a Unique Terminal Nucleotide Sequence" Bioorganic Chemistry (1986) 12(6): 842-845.
Mandecki, et al., "FokI method of gene synthesis" Gene (1988) 68: 101-107.
Mormeneo, et al., "Precise nucleotide sequence modifications with bidirectionally cleaving class-IIS excision linkers" Gene (1987) 61: 21-30.
Palzkill, et al., "Probing β-Lactamase Structure and Function Using Random Replacement Mutagenesis" Proteins (1992) 14: 29-44.
Poustka, et al., "Construction and use of human chromosome jumping libraries from NotI-digested DNA" Nature (1987) 325: 353-355.
Szybalski, et al., "Class-IIS restriction enzymes—a review" Gene (1991) 100: 13-26.
Life Technologies' Answer and Defenses to Defendants', Illumina and Solexa's, Counterclaims and Counter-counterclaims, dated Nov. 5, 2009, in the matter of Life Technologies Corp. v. Illumina, Inc., 09-706 RK, U.S. District Court for the District of Delaware.
Life Technologies' Responses to Illumina and Solexa's First Set of Interrogatories, dated Dec. 21, 2009, in the matter of Life Technologies Corp. v. Illumina, Inc., 09-706 RK, U.S. District Court for the District of Delaware.
Life Technologies' Amended Answer and Defenses to Defendants', Illumina and Solexa's, Counterclaims and Counter-counterclaims, dated Jan. 29, 2010, in the matter of Life Technologies Corp. v. Illumina, Inc., 09-706 RK, U.S. District Court for the District of Delaware.
Illumina and Solexa's Answer to the Amended Counter-counterclaims of Life Technologies, dated Feb. 12, 2010, in the matter of Life Technologies Corp. v. Illumina, Inc., 09-706 RK, U.S. District Court for the District of Delaware.
Life Technologies' First Supplemental Response to Illumina and Solexa's Interrogatories Nos. 2, 3, 8, and 10, dated Feb. 26, 2010, in the matter of Life Technologies Corp. v. Illumina, Inc., 09-706 RK, U.S. District Court for the District of Delaware.
Exhibit A (Claim Charts Aligning References to the Claims of U.S. Patent No. 6,554,505) to Life Technologies' First Supplemental Response to Illumina and Solexa's Interrogatories Nos. 2, 3, 8, and 10, dated Feb. 26, 2010, in the matter of Life Technologies Corp. v. Illumina, Inc., 09-706 RK, U.S. District Court for the District of Delaware.
Exhibit B (Claim Charts Aligning References to the Claims of U.S. Patent No. 6,831,994) to Life Technologies' First Supplemental Response to Illumina and Solexa's Interrogatories Nos. 2, 3, 8, and 10, dated Feb. 26, 2010, in the matter of Life Technologies Corp. v. Illumina, Inc., 09-706 RK, U.S. District Court for the District of Delaware.
Life Technologies' Revised First Supplemental Response to Illumina and Solexa's Interrogatories Nos. 2, 3, 8, and 10, dated Feb. 26, 2010, in the matter of Life Technologies Corp. v. Illumina, Inc., 09-706 RK, U.S. District Court for the District of Delaware.
Exhibit A (Claim Charts Aligning References to the Claims of U.S. Patent No. 6,554,505) to Life Technologies' Revised First Supplemental Response to Illumina and Solexa's Interrogatories Nos. 2, 3, 8, and 10, dated Feb. 26, 2010, in the matter of Life Technologies Corp. v. Illumina, Inc., 09706 RK, U.S. District Court for the District of Delaware.
Exhibit B (Claim Charts Aligning References to the Claims of U.S. Patent No. 6,831,994) to Life Technologies' Revised First Supplemental Response to Illumina and Solexa's Interrogatories Nos. 2, 3,

(56) References Cited

OTHER PUBLICATIONS 8, and 10, dated Feb. 26, 2010, in the matter of *Life Technologies Corp.* v. *Illumina, Inc.*, 09706 RK, U.S. District Court for the District of Delaware.
Joint Claim Construction Chart and Statement, in the matter of *Life Technologies Corp.* v. *Illumina, Inc.*, 09-706 RK, U.S. District Court for the District of Delaware, dated May 7, 2010.
Exhibit A (Stipulated Constructions for Identified Terms in the Patents-In-Suit) to Amended Joint Claim Construction Chart and Statement, in the matter of *Life Technologies Corp.* v. *Illumina, Inc.*, 09-706 RK, U.S. District Court for the District of Delaware, dated May 13, 2010.
Exhibit B (Proposed Constructions for Identified Terms) to Amended Joint Claim Construction Chart and Statement, in the matter of *Life Technologies Corp.* v. *Illumina, Inc.*, 09-706 RK, U.S. District Court for the District of Delaware, dated May 7, 2010.
Amended Joint Claim Construction Chart and Statement, in the matter of *Life Technologies Corp.* v. *Illumina, Inc.*, 09-706 RK, U.S. District Court for the District of Delaware, dated May 13, 2010.
Amended Exhibit A (Stipulated Constructions for Identified Terms in the Patents-In-Suit) to Amended Joint Claim Construction Chart and Statement, in the matter of *Life Technologies Corp.* v. *Illumina, Inc.*, 09-706 RK, U.S. District Court for the District of Delaware, dated May 13, 2010.
Amended Exhibit B (Proposed Constructions for Identified Terms) to Amended Joint Claim Construction Chart and Statement, in the matter of *Life Technologies Corp.* v. *Illumina, Inc.*, 09-706 RK, U.S. District Court for the District of Delaware, dated May 13, 2010.
Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit A (Oxford Dictionary of Biochemistry and Microbiology) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit B (Glossary of Chemical Terms) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit C (McGraw-Hill Dictionary of Chemistry) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit D (Grant & Hackh's Chemical Dictionary) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit E (Dictionary.com) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit F (McGraw-Hill Dictionary of Scientific and Technical Terms) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit G (Webster's Third New International Dictionary) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit H (Roget's 21s Century Thesaurus) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit I (U.S. Pat. No. 4,125,828) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit J (Academic Press Dictionary of Science and Technology) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit K (Dictionary.com) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Life Technologies' Opening Claim Construction Brief, dated May 27, 2010, in the matter of *Life Technologies Corp.* v. *Illumina, Inc.*, 09-706 RK, U.S. District Court fot the District of Delaware.
Exhibit A (Exemplary Claim Terms) to Life Technologies' Opening Claim Construction Brief, dated May 27, 2010, in the matter of *Life Technologies Corp.* v. *Illumina, Inc.*, 09-706 RK, U.S. District Court for the District of Delaware.
Exhibit B (Amendment and Response to Office Action in Inter Partes Reexamination, filed May 21, 2010 in Reexamination Control No. 95/001,292) to Life Technologies' Opening Claim Construction Brief, dated May 27, 2010, in the matter of *Life Technologies Corp.* v. *Illumina, Inc.*, 09-706 RK, U.S. District Court for the District of Delaware.
Exhibit C (Amendment and Reply to Office Action in Inter Partes Reexamination, filed May 21, 2010 in Reexamination Control No. 95/000,527) to Life Technologies' Opening Claim Construction Brief, dated May 27, 2010, in the matter of *Life Technologies Corp.* v. *Illumina, Inc.*, 09-706 RK, U.S. District Court for the District of Delaware.
Exhibit D (American Heritage Dictionary of the English Language) to Life Technologies' Opening Claim Construction Brief, dated May 27, 2010, in the matter of *Life Technologies Corp.* v. *Illumina, Inc.*, 09-706 RK, U.S. District Court for the District of Delaware.
Exhibit E (the Merriam-Webster Dictionary) to Life Technologies' Opening Claim Construction Brief, dated May 27, 2010, in the matter of *Life Technologies Corp.* v. *Illumina, Inc.*, 09-706 RK, U.S. District Court for the District of Delaware.
Exhibit F (Concise Dictionary of Biomedicine and Molecular Biology) to Life Technologies' Opening Claim Construction Brief, dated May 27, 2010, in the matter of *Life Technologies Corp.* v. *Illumina, Inc.*, 09-706 RK, U.S. District Court for the District of Delaware.
Exhibit G (Human Molecular Genetics 2) to Life Technologies' Opening Claim Construction Brief, dated May 27, 2010, in the matter of *Life Technologies Corp.* v. *Illumina, Inc.*, 09-706 RK, U.S. District Court for the District of Delaware.
Exhibit H (Amendment filed Feb. 2, 2006 in Application No. 10/706,118) to Life Technologies' Opening Claim Construction Brief, dated May 27, 2010, in the matter of *Life Technologies Corp.* v. *Illumina, Inc.*, 09-706 RK, U.S. District Court for the District of Delaware.
Exhibit I (Classification Definitions) to Life Technologies' Opening Claim Construction Brief, dated May 27, 2010, in the matter of *Life Technologies Corp.* v. *Illumina, Inc.*, 09-706 RK, U.S. District Court for the District of Delaware.
Exhibit J (Nova Online: Cracking the Code of Life: Fragmentation of Chromosomes) to Life Technologies' Opening Claim Construction Brief, dated May 27, 2010, in the matter of *Life Technologies Corp.* v. *Illumina, Inc.*, 09-706 RK, U.S. District Court for the District of Delaware.
Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

(56) References Cited

OTHER PUBLICATIONS

Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.
Exhibit A (Chetverina and Chetverin) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.
Exhibit B (Molecular Biology of the Cell) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.
Exhibit C (Sakai et al.) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.
Exhibit D (WO 91/07486) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.
Exhibit E (Applied Biosytsems Solid 4 System Sets Software) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.
Exhibit F (Applied Biosytsems SOLID EZ Bead System) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.
Exhibit G (Amendment and Response to Office Action in Inter Partes Reexamination, filed May 21, 2010 in Reexamination Control No. 95/001,292) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.
Exhibit H (Comments by Third Party Requester to Patent Owner's Amendment and Reply to Office Action in Inter Partes Reexamination, filed Jun. 21, 2010 in Reexamination Control No. 95/000,527) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.
Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit A (Academic Press Dictionary of Science and Technology) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit B (American Heritage Dictionary of the English Language) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit C (*Arbitron* v. *International Demographics, Inc.*) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit D (Webster's Third New International Dictionary) to Life Technologies' Responsive Claim Construction Brief, dated Jun. 25, 2010, in the matter of *Life Technologies Corp.* v. *Illumina, Inc.*, 09706 RK, U.S. District Court for the District of Delaware.
Exhibit E (Roget's 21st Century Thesaurus) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit F (Substitute Petition to the Director under 37 C.F.R. § 1.78, filed Jun. 17, 2010 in Reexamination Control No. 95/001,292) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware
Exhibit G (Oxford Dictionary of Biochemistry and Molecular Biology) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit H (Webster's Third New International Dictionary) to Life Technologies' Responsive Claim Construction Brief, dated Jun. 25, 2010, in the matter of *Life Technologies Corp.* v. *Illumina, Inc.*, 09706 RK, U.S. District Court for the District of Delaware.
Exhibit I (Dictionary.com) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit J (Academic Press Dictionary of Science and Technology) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit K (The American Heritage Dictionary of the English Language) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit L (The Merriam-Webster Dictionary) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit M (*Vizio, Inc.* v. *International Trade Commission*) to Life Technologies' Responsive Claim Construction Brief, dated Jun. 25, 2010, in the matter of *Life Technologies Corp.* v. *Illumina, Inc.*, 09706 RK, U.S. District Court for the District of Delaware.
Joint Appendix for Claim Construction Briefs, in the matter of *Life Technologies Corp.* v. *Illumina, Inc.*, 09-706 RK, U.S. District Court for the District of Delaware, dated Jul. 1, 2010.
Cited Documents in Joint Appendix for Claim Construction Briefs, in the matter of *Life Technologies Corp.* v. *Illumina, Inc.*, 09-706 RK, U.S. District Court for the District of Delaware, dated Jul. 1, 2010.
Illumina's Slides for Markman Hearing for U.S. Patent Nos. 6,831,994 and 6,554,505, in the matter of *Life Technologies Corp.* v. *Illumina, Inc.*, 09-706 RK, U.S. District Court for the District of Delaware, dated Jul. 26, 2010.
Life Technologies' Slides for Markman Hearing for U.S. Patent Nos. 6,831,994 and 6,554,505, in the matter of *Life Technologies Corp.* v. *Illumina, Inc.*, 09-706 RK, U.S. District Court for the District of Delaware, dated Jul. 26, 2010.
Illumina's Slides for Markman Hearing for U.S. Patent No. 7,598,035, in the matter of *Life Technologies Corp.* v. *Illumina, Inc.*, 09-706 RK, U.S. District Court for the District of Delaware, dated Jul. 26, 2010.

\* cited by examiner

SEQUENCE LISTING

<160> NUMBER OF SEQ ID NOS: 8

<210> SEQ ID NO 1
<211> LENGTH: 40
<212> TYPE: DNA
<213> ORGANISM: Artificial Sequence
<220> FEATURE:
<223> OTHER INFORMATION: Example sequence
<220> FEATURE:
<221> NAME/KEY: variation
<222> LOCATION: (1)...(40)
<223> OTHER INFORMATION: N = A, C, G, T

<400> SEQUENCE: 1
nnnnnnnnnn nnnnnnnnnn nnnnnnnnnn nnnnnnnnnn                            40

<210> SEQ ID NO 2
<211> LENGTH: 36
<212> TYPE: DNA
<213> ORGANISM: Artificial Sequence
<220> FEATURE:
<223> OTHER INFORMATION: Example sequence

<400> SEQUENCE: 2
aattagccgt acctgcagca gtgcagaagc ttgcgt                                36

<210> SEQ ID NO 3
<211> LENGTH: 36
<212> TYPE: DNA
<213> ORGANISM: Artificial Sequence
<220> FEATURE:
<223> OTHER INFORMATION: Example sequence

<400> SEQUENCE: 3
aaacctcaga attcctgcac agctgcgaat cattcg                                36

<210> SEQ ID NO 4
<211> LENGTH: 36
<212> TYPE: DNA
<213> ORGANISM: Artificial Sequence
<220> FEATURE:
<223> OTHER INFORMATION: Example sequence

<400> SEQUENCE: 4
agctcgaatg attcgcagct gtgcaggaat tctgag                                36

<210> SEQ ID NO 5
<211> LENGTH: 36
<212> TYPE: DNA
<213> ORGANISM: Artificial Sequence
<220> FEATURE:
<223> OTHER INFORMATION: Example sequence

<400> SEQUENCE: 5
gtttacgcaa gcttctgcac tgctgcaggt acggct                                36

<210> SEQ ID NO 6
<211> LENGTH: 72
<212> TYPE: DNA
<213> ORGANISM: Artificial Sequence
<220> FEATURE:
<223> OTHER INFORMATION: Example sequence

<400> SEQUENCE: 6
aattagccgt acctgcagca gtgcagaagc ttgcgtaaac ctcagaattc ctgcacagct      60
gcgaatcatt cg                                                          72

```
<210> SEQ ID NO 7
<211> LENGTH: 72
<212> TYPE: DNA
<213> ORGANISM: Artificial Sequence
<220> FEATURE:
<223> OTHER INFORMATION: Example sequence

<400> SEQUENCE: 7
agctcgaatg attcgcagct gtgcaggaat tctgaggttt acgcaagctt ctgcactgct      60
gcaggtacgg ct                                                         72

<210> SEQ ID NO 8
<211> LENGTH: 49
<212> TYPE: DNA
<213> ORGANISM: Artificial Sequence
<220> FEATURE:
<223> OTHER INFORMATION: Example Sequence

<400> SEQUENCE: 8
gttgggtcaa caaattacct tattgtaacc ttcgcattag ccggagcct                 49
```

METHODS FOR SEQUENCING POLYNUCLEOTIDES

RELATED U.S. APPLICATIONS

This application is a continuation of application Ser. No. 13/622,273, filed Sep. 18, 2012, now U.S. Pat. No. 8,557,521 issued Oct. 15, 2013, which is a continuation of application Ser. No. 12/558,396, filed Sep. 11, 2009, now U.S. Pat. No. 8,288,095 issued Oct. 16, 2012, which is a continuation of application Ser. No. 10/962,337, filed on Oct. 8, 2004, now U.S. Pat. No. 7,598,035 issued Oct. 6, 2009, which is a divisional of application Ser. No. 10/706,118 filed on Nov. 12, 2003, now abandoned, which is a divisional of application Ser. No. 09/549,748 filed on Apr. 14, 2000, now U.S. Pat. No. 6,720,179 issued Apr. 13, 2004, which is a divisional of application Ser. No. 09/028,128 filed on Feb. 23, 1998, now U.S. Pat. No. 6,054,276 issued Apr. 25, 2000, all of which are incorporated herein by reference in their entirety.

FIELD OF THE INVENTION

The invention relates generally to methods for construction physical maps of DNA, especially genomic DNA, and more particularly, to a method of providing high resolution physical maps by sequence analysis of concatenations of segments of restriction fragment ends.

BACKGROUND OF THE INVENTION

Physical maps of one or more large pieces of DNA, such as a genome or chromosome, consist of an ordered collection of molecular landmarks that may be used to position, or map, a smaller fragment, such as clone containing a gene of interest, within the larger structure, e.g. U.S. Department of Energy, "Primer on Molecular Genetics," from Human Genome 1991-92 Program Report; and Los Alamos Science, 20: 112-122 (1992). An important goal of the Human Genome Project has been to provide a series of genetic and physical maps of the human genome with increasing resolution, i.e. with reduced distances in basepairs between molecular landmarks, e.g. Murray et al, Science, 265: 2049-2054 (1994); Hudson et al, Science, 270: 1945-1954 (1995); Schuler et al, Science, 274: 540-546 (1996); and so on. Such maps have great value not only in furthering our understanding of genome organization, but also as tools for helping to fill contig gaps in large-scale sequencing projects and as tools for helping to isolate disease-related genes in positional cloning projects, e.g. Rowen et al, pages 167-174, in Adams et al, editors, Automated DNA Sequencing and Analysis (Academic Press, New York, 1994); Collins, Nature Genetics, 9: 347-350 (1995); Rossiter and Caskey, Annals of Surgical Oncology, 2: 14-25 (1995); and Schuler et al (cited above). In both cases, the ability to rapidly construct high-resolution physical maps of large pieces of genomic DNA is highly desirable.

Two important approaches to genomic mapping include the identification and use of sequence tagged sites (STS's), e.g. Olson et al, Science, 245: 1434-1435 (1989); and Green et al, PCR Methods and Applications, 1: 77-90 (1991), and the construction and use of jumping and linking libraries, e.g. Collins et al, Proc. Natl. Acad. Sci., 81: 6812-6816 (1984); and Poustka and Lehrach, Trends in Genetics, 2: 174-179 (1986). The former approach makes maps highly portable and convenient, as maps consist of ordered collections of nucleotide sequences that allow application without having to acquire scarce or specialized reagents and libraries. The latter approach provides a systematic means for identifying molecular landmarks spanning large genetic distances and for ordering such landmarks via hybridization assays with members of a linking library.

Unfortunately, these approaches to mapping genomic DNA are difficult and laborious to implement. It would be highly desirable if there was an approach for constructing physical maps that combined the systematic quality of the jumping and linking libraries with the convenience and portability of the STS approach.

SUMMARY OF THE INVENTION

Accordingly, an object of my invention is to provide methods and materials for constructing high resolution physical maps of genomic DNA.

Another object of my invention is to provide a method of ordering restriction fragments from multiple enzyme digests by aligning matching sequences of their ends.

Still another object of my invention is to provide a high resolution physical map of a target polynucleotide that permits directed sequencing of the target polynucleotide with the sequences of the map.

Another object of my invention is to provide vectors for excising ends of restriction fragments for concatenation and sequencing.

Still another object of my invent is to provide a method monitoring the expression of genes.

A further object of my invention is to provide physical maps of genomic DNA that consist of an ordered collection of nucleotide sequences spaced at an average distance of a few hundred to a few thousand bases.

My invention achieves these and other objects by providing methods and materials for determining the nucleotide sequences of both ends of restriction fragments obtained from multiple enzymatic digests of a target polynucleotide, such as a fragment of a genome, or chromosome, or an insert of a cosmid, BAC, YAC, or the like. In accordance with the invention, a polynucleotide is separately digested with different combinations of restriction endonucleases and the ends of the restriction fragments are sequenced so that pairs of sequences from each fragment are produced. A physical map of the polynucleotide is constructed by ordering the pairs of sequences by matching the identical sequences among such pairs resulting from all of the digestions.

In the preferred embodiment, a polynucleotide is mapped by the following steps: (a) providing a plurality of populations of restriction fragments, the restriction fragments of each population having ends defined by digesting the polynucleotide with a plurality of combinations of restriction endonucleases; (b) determining the nucleotide sequence of a portion of each end of each restriction fragment of each population so that a pair of nucleotide sequences is obtained for each restriction fragment of each population; and (c) ordering the pairs of nucleotide sequences by matching the nucleotide sequences between pairs to form a map of the polynucleotide.

Another aspect of the invention is the monitoring gene expression by providing pairs of segments excised from cDNAs. In this embodiment, segments from each end of each cDNA of a population of cDNAs are ligated together to form pairs, which serve to identify their associated cDNAs. Concatenations of such pairs are sequenced by conventional techniques to provide information on the relative frequencies of expression in the population.

The invention provides a means for generating a high density physical map of target polynucleotides based on the positions of the restriction sites of predetermined restriction endonucleases. Such physical maps provide many advantages, including a more efficient means for directed sequencing of large DNA fragments, the positioning of expression sequence tags and cDNA sequences on large genomic fragments, such as BAC library inserts, thereby making positional candidate mapping easier; and the like.

DEFINITIONS

Figure 1:
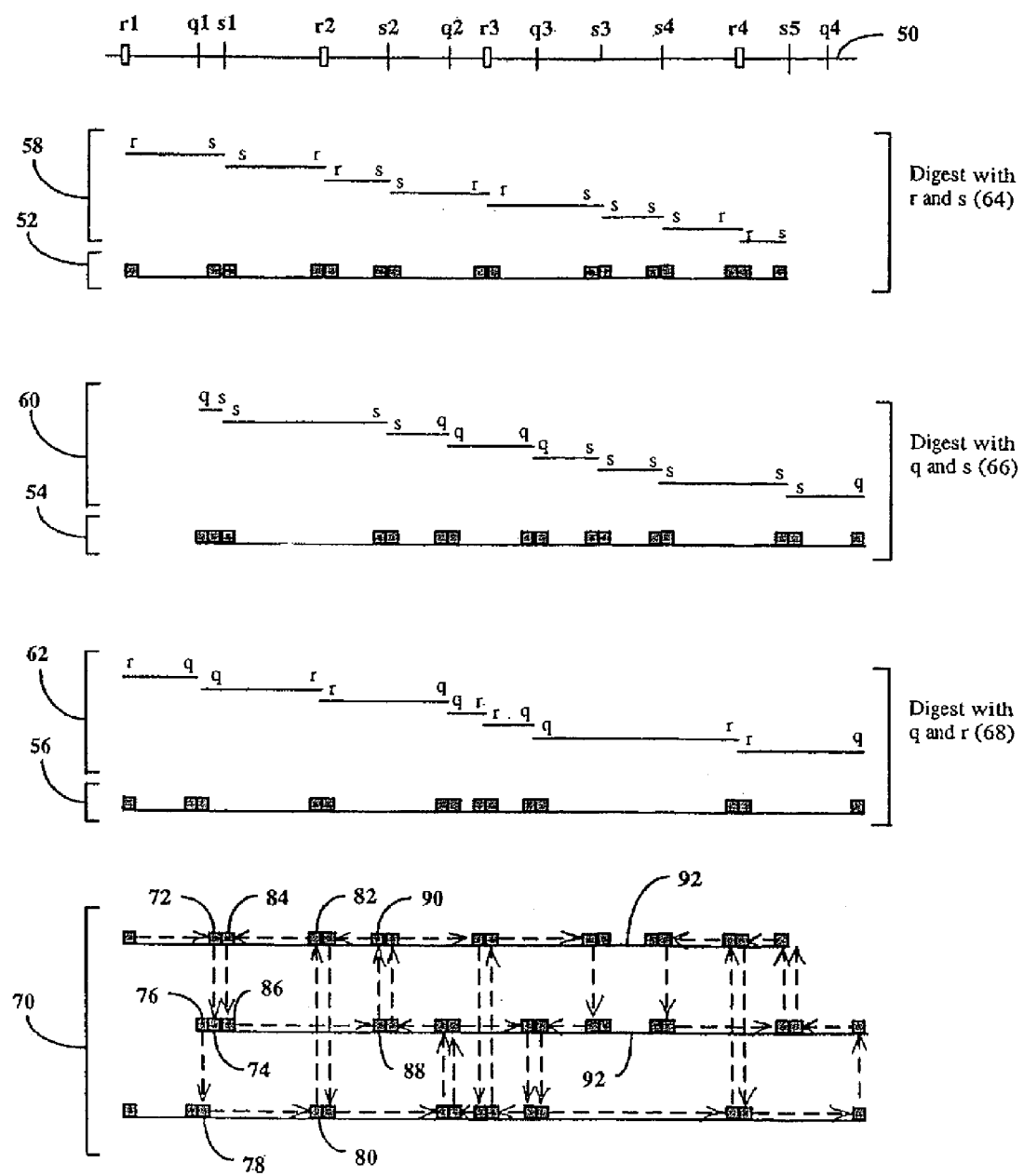
FIG. 1 graphically illustrates the concept of a preferred embodiment of the invention.

As used herein, the process of "mapping" a polynucleotide means providing a ordering, or series, of sequenced segments of the polynucleotide that correspond to the actual ordering of the segments in the polynucleotide. For example, the following set of five-base sequences is a map of the polynucleotide below (SEQ ID NO: 8), which has the ordered set of sequences making up the map underlined:

(gggtc, ttatt, aacct, catta, ccgga)

GTT<u>GGGTC</u>AACAAATTACC<u>TTATT</u>GT<u>AACCT</u>TCG<u>CATTA</u>G<u>CCGGA</u>GCCT

The term "oligonucleotide" as used herein includes linear oligomers of natural or modified monomers or linkages, including deoxyribonucleosides, ribonucleosides, and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 34, to several tens of monomeric units, e.g. 40-60. Whenever an oligonucleotide is represented by a sequence of letters, such as "ATGCCTG," it will be understood that the nucleotides are in 5'.fwdarw.3' order from left to right and that "A" denotes deoxyadenosine, "C" denotes deoxycytidine, "G" denotes deoxyguanosine, and "T" denotes ihymidine, unless otherwise noted. Usually oligonucleotides comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oigonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the only proviso that they are capable of specific hybridization. Such analogs include synthetic nucleosides designed to enhance binding properties, reduce complexity, increase specificity, and the like.

As used herein, the term "complexity" in reference to a population of polynucleotides means the number of different species of polynucleotide present in the population.

DETAILED DESCRIPTION OF THE PREFERRED EMBODIMENT

In accordance with the present invention, segments of nucleotides at each end of restriction fragments produced from multiple digestions of a polynucleotide are sequenced and used to arrange the fragments into a physical map. Such a physical map consists of an ordered collection of the nucleotide sequences of the segments immediately adjacent to the cleavage sites of the endonucleases used in the digestions. Preferably, after each digestion, segments are removed from the ends of each restriction fragment by cleavage with a type IIs restriction endonuclease. Excised segments from the same fragment are ligated together to form a pair of segments. Preferably, collections of such pairs are concatenated by ligation, cloned, and sequenced using conventional techniques.

The concept of the invention is illustrated in FIG. 1 for an embodiment which employs three restriction endonucleases: r, q, and s. Polynucleotide (50) has recognition sites ($r_1, r_2, r_3$, and $r_4$) for restriction endonucleases r, recognition sites ($q_1$ through $q_4$) for restriction endonuclease q, and recognition sites ($s_1$ through $s_5$) for restriction endonuclease s. In accordance with the preferred embodiment, polynucleotide (50) is separately digested with r and s, q and s, and r and q to produce three populations of restriction fragments (58), (60), and (62), respectively. Segments adjacent to the ends of each restriction fragment are sequenced to form sets of pairs (52), (54), and (56) of nucleotide sequences, which for sake of illustration are shown directly beneath their corresponding restriction fragments in the correct order. Pairs of sequences from all three sets are ordered by matching sequences between pairs as shown (70). A nucleotide sequence (72) from a first pair is matched with a sequence (74) of a second pair whose other sequence (76), in turn, is matched with a sequence (78) of a third pair. The matching continues, as (80) is matched with (82), (84) with (86), (88) with (90), and so on, until the maximum number of pairs are included. It is noted that some pairs (92) do not contribute to the map. These correspond to fragments having the same restriction site at both ends. In other word, they correspond to situations where there are two (or more) consecutive restriction sites of the same type without other sites in between, e.g. $s_3$ and $s_4$ in this example. Preferably, algorithms used for assembling a physical map from the pairs of sequences can eliminate pairs having identical sequences.

Generally, a plurality of enzymes is employed in each digestion. Preferably, at least three distinct recognition sites are used. This can be accomplished by using three or more restriction endonucleases, such as Hind III, Eco RI, and Xba I, which recognize different nucleotide sequences, or by using restriction endonucleases recognizing the same nucleotide sequence, but which have different methylation sensitivities. That is, it is understood that a different "recognition site" may be different solely by virtue of a different methylation state. Preferably, a set of at least three recognition endonucleases is employed in the method of the invention. From this set a plurality of combinations of restriction endonucleases is formed for separate digestion of a target polynucleoitde. Preferably, the combinations are "n−1" combinations of the set. In other words, for a set of n restriction endonucleases, the preferred combinations are all the combinations of n−1 restriction endonucleases. For example, as illustrated in FIG. 1 where a set of three restriction endonucleases (r, q, and s) are employed, the n−1 combinations are (r, q), (r, s), and (q, s). Likewise, if four restriction endonucleases (r, q, s, and w) are employed, the n−1 combinations are (r, q, s), (r, q, w), (r, s, w), and (q, s, w). It is readily seen that where a set of n restriction endonucleases are employed the plurality of n−1 combinations is n.

Figure 2:
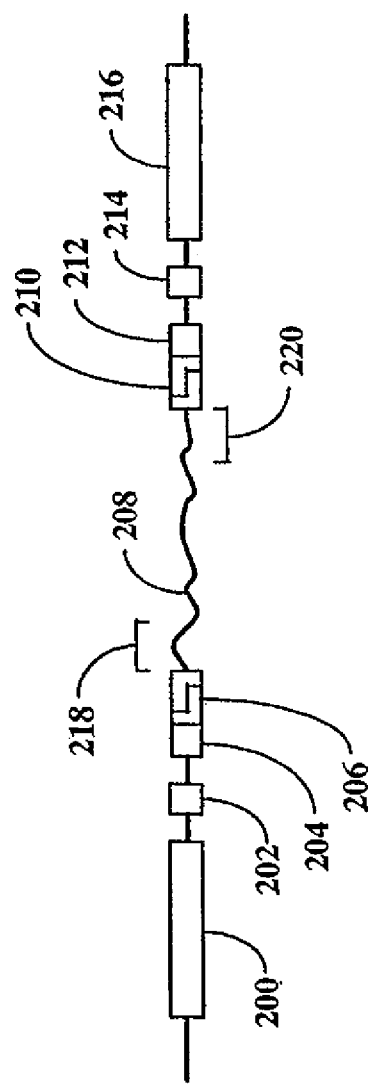
FIG. 2 provides a diagram of a vector for forming pairs of nucleotide sequences in accordance with a preferred embodiment of the invention.

Preferably, the method of the invention is carried out using a vector, such as that illustrated in FIG. 2. The vector is readily constructed from commercially available materials using conventional recombinant DNA techniques, e.g. as disclosed in Sambrook et al, Molecular Cloning, Second Edition (Cold Spring Harbor Laboratory, New York, 1989). Preferably, pUC-based plasmids, such as pUC19, or .lambda.-based phages, such as .lambda. ZAP Express (Stratagene Cloning Systems, La Jolla, Calif.), or like vectors are employed. Important features of the vector are recognition sites (204) and (212) for two type IIs restriction endonucleases that flank restriction fragment (208). For convenience, the two type IIs restriction enzymes are referred to herein as "IIs$_1$" and "IIs$_2$", respectively. IIs$_1$ and IIs$_2$ may be the same or different. Recognition sites (204) and (212) are oriented so that the cleavage sites of IIs$_1$ and IIs$_2$ are located in the interior of restriction fragment (208). In other words, taking the 5' direction as "upstream" and the 3' direction as "downstream," the cleavage site of IIs$_1$ is downstream of its recognition site and the cleavage site of IIs$_2$ is upstream of its recognition site. Thus, when the vector is cleaved with IIs$_1$ and IIs$_2$ two segments (218) and (220) of restriction fragment (208) remain attached to the vector. The vector is then re-circularized by ligating the two ends together, thereby forming a pair of segments. If such cleavage results in one or more single stranded overhangs, i.e. one or more non-blunt ends, then the ends are preferably rendered blunt prior to re-circularization, for example, by digesting the protruding strand with a nuclease such as Mung bean nuclease, or by extending a 3' recessed strand, if one is produced in the digestion. The ligation reaction for re-circularization is carried out under conditions that favor the formation of covalent circles rather than concatemers of the vector. Preferably, the vector concentration for the ligation is between about 0.4 and about 4.0 μg/ml of vector DNA, e.g. as disclosed in Collins et al, Proc. Natl. Acad. Sci., 81: 6812-6812 (1984), for .alpha.-based vectors. For vectors of different molecular weight, the concentration range is adjusted appropriately.

In the preferred embodiments, the number of nucleotides identified depends on the "reach" of the type IIs restriction endonucleases employed. "Reach" is the amount of separation between a recognition site of a type IIs restriction endonuclease and its cleavage site, e.g. Brenner, U.S. Pat. No. 5,559,675. The conventional measure of reach is given as a ratio of integers, such as "(16/14)", where the numerator is the number of nucleotides from the recognition site in the 5' to 3' direction that cleavage of one strand occurs and the denominator is the number of nucleotides from the recognition site in the 3' to 5' direction that cleavage of the other strand occurs. Preferred type IIs restriction endonucleases for use as IIs$_1$ and IIs$_2$ in the preferred embodiment include the following: Bbv I, Bce 83 I, Bcef I, Bpm I, Bsg I, BspLU II III, Bst 71 I, Eco 57 I, Fok I, Gsu I, Hga I, Mme I, and the like. In the preferred embodiment, a vector is selected which does not contain a recognition site, other than (204) and (212), for the type IIs enzyme(s) used to generate pairs of segments; otherwise, re-circularization cannot be carried out.

Preferably, a type IIs restriction endonuclease for generating pairs of segments has as great a reach as possible to maximize the probability that the nucleotide sequences of the segments are unique. This in turn maximizes the probability that a unique physical map can be assembled. If the target polynucleotide is a bacterial genome of 1 megabase, for a restriction endonuclease with a six basepair recognition site, about 250 fragments are generated (or about 500 ends) and the number of nucleotides determined could be as low as five or six, and still have a significant probability that each end sequence would be unique. Preferably, for polynucleotides less than or equal to 10 megabases, at least 8 nucleotides are determined in the regions adjacent to restriction sites, when a restriction endonuclease having a six basepair recognition site is employed. Generally for polynucleotides less than or equal to 10 megabases, 9-12 nucleotides are preferably determined to ensure that the end sequences are unique. In the preferred embodiment, type IIs enzymes having a (16/14) reach effectively provide 9 bases of unique sequence (since blunting reduces the number of bases to 14 and 5 bases are part of the recognition sites (206) or (210)). In a polynucleotide having a random sequence of nucleotides, a 9-mer appears on average about once every 262,000 bases. Thus, 9-mer sequences are quite suitable for uniquely labeling restriction fragments of a target polynucleotide corresponding to a typical yeast artificial chromosome (YACs) insert, i.e. 100-1000 kilobases, bacterial artificial chromosome (BAC) insert, i.e. 50-250 kilobases, and the like.

Immediately adjacent to IIs sites (204) and (212) are restriction sites (206) and (210), respectively that permit restriction fragment (208) to be inserted into the vector. That is, restriction site (206) is immediately downstream of (204) and (210) is immediately upstream of (212). Preferably, sites (204) and (206) are as close together as possible, even overlapping, provided type IIs site (206) is not destroyed upon cleavage with the enzymes for inserting restriction fragment (208). This is desirable because the recognition site of the restriction endonuclease used for generating the fragments occurs between the recognition site and cleavage site of type IIs enzyme used to remove a segment for sequencing, i.e. it occurs within the "reach" of the type IIs enzyme. Thus, the closer the recognition sites, the larger the piece of unique sequence can be removed from the fragment. The same of course holds for restriction sites (210) and (212). Preferably, whenever the vector employed is based on a pUC plasmid, restriction sites (206) and (210) are selected from either the restriction sites of polylinker region of the pUC plasmid or from the set of sites which do not appeal in the pUC. Such sites include Eco RI, Apo I, Ban II, Sac I, Kpn I, Acc65 I, Ava I, Xma I, Sma I, Bam HI, Xba I, Sal I, Hinc II, Acc I, BspMI, Pst I, Sse8387 I, Sph I, Hind III, Afl II, Age I, Bsp120 I, Asc I, Bbs I, Bcl I, Bgl II, Blp I, BsaA I, Bsa BI, Bse RI, Bsm I, Cla I, Bsp EI, BssH II, Bst BI, BstXI, Dra III, Eag I, Eco RV, Fse I, Hpa I, Mfe I, Nae I, Nco I, Nhe I, Not I, Nru I, Pac I, Xho I, Pme I, Sac II, Spe I, Stu I, and the like. Preferably, six-nucleotide recognition sites (i.e. "6-cutters") are used, and more preferably, 6-cutters leaving four-nucleotide protruding strands are used.

Preferably, the vectors contain primer binding sites (200) and (216) for primers $p_1$ and $p_2$, respectively, which may be used to amplify the pair of segments by PCR after re-circularization. Recognition sites (202) and (214) are for restriction endonucleases $w_1$ and $w_2$, which are used to cleave the pair of segments from the vector after amplification. Preferably, $w_1$ and $w_2$, which may be the same or different, are type IIs restriction endonucleases whose cleavage sites correspond to those of (206) and (210), thereby removing surplus, or non-informative, sequence (such as the recognition sites (204) and (212)) and generating protruding ends that permit concatenation of the pairs of segments.

Figure 3:
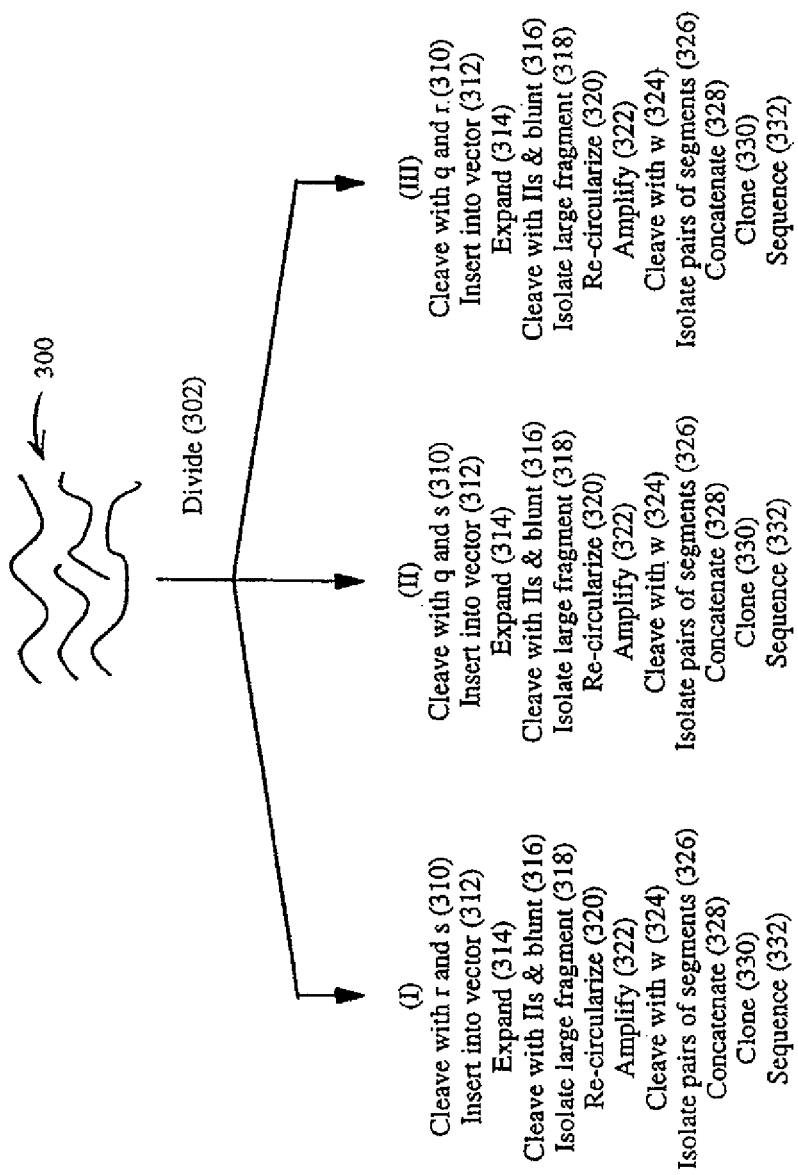
FIG. 3 illustrates a scheme for carrying out the steps of a preferred embodiment of the invention.

FIG. 3 illustrates steps in a preferred method using vectors of FIG. 2. Genomic or other DNA (400) is obtained using conventional techniques, e.g. Herrmann and Frischauf, Methods in Enzymology, 152: 180-183 (1987); Frischauf, Methods in Enzymology, 152: 183-199 (1987), or the like, after which it is divided (302) into aliquots that are separately digested (310) with combinations restriction endonucleases, as shown in FIG. 3 for the n−1 combinations of the set of enzymes r, s, and q. Preferably, the resulting fragments are treated with a phosphatase to prevent ligation of the genomic fragments with one another before or during insertion into a vector. Restriction fragments are inserted (312) into vectors designed with cloning sites to specifically accept the fragments. That is, fragments digested with r and s are inserted into a vector that accepts r-s fragments. Fragments having the same ends, e.g. r-r and s-s, are not cloned since information derived from them does not contribute to the map. r-s fragments are of course inserted into the vector in both orientations. Thus, for a set of three restriction endonucleases, only three vectors are required, e.g. one each for accepting r-s, r-q, and s-q fragments. Likewise, for a set of four restriction endonucleases, e.g. r, s, q, and t, only six vectors are required, one each for accepting r-s, r-q, r-t, s-q, s-t, and q-t fragments.

After insertion, a suitable host is transformed with the vectors and cultured, i.e. expanded (314), using conventional techniques. Transformed host cells are then selected, e.g. by plating and picking colonies using a standard marker, e.g. .beta.-glactosidase/X-gal. A large enough sample of transformed host cells is taken to ensure that every restriction fragment is present for analysis with a reasonably large probability. This is similar to the problem of ensuring representation of a clone of a rare mRNA in a cDNA library, as discussed in Sambrook et al, Molecular Cloning, Second Edition (Cold Spring Harbor Laboratory, New York, 1989), and like references. Briefly, the number of fragments, N, that must be in a sample to achieve a given probability, P, of including a given fragment is the following: $N = \ln(1-P)/\ln(1-f)$, where f is the frequency of the fragment in the population. Thus, for a population of 500 restriction fragments, a sample containing 3454 vectors will include at least one copy of each fragment (i.e. a complete set) with a probability of 99.9%; and a sample containing 2300 vectors will include at least one copy of each fragment with a probability of 99%. The table below provides the results of similar calculations for target polynucleotides of different sizes:

TABLE 1

| Size of Target Polynucleotide (basepairs) | Average fragment size after cleavage with 2 six-cutters (No. of gragments) [Sample size for complete set with 99% probability] | Average fragment size after cleavage with 3 six-cutters (No. of fragments) [Sample size for complete set with 99% probability] |
| --- | --- | --- |
| $2.5 \times 10^5$ | 2048 (124) [576] | 1365 (250) [1050] |
| $5 \times 10^5$ | 2048 (250) [1050] | 1365 (500) [2300] |
| $1 \times 10^6$ | 2048 (500) [2300] | 1365 (1000) [4605] |

After selection, the vector-containing hosts are combined and expanded in cultured. The vectors are then isolated, e.g. by a conventional mini-prep, or the like, and cleaved with $IIs_1$ and $IIs_2$ (316). The fragments comprising the vector and ends (i.e. segments) of the restriction fragment insert are isolated, e.g. by gel electrophoresis, blunted (316), and re-circularized (320). The resulting pairs of segments in the re-circularized vectors are then amplified (322), e.g. by polymerase chain reaction (PCR), after which the amplified pairs are cleaved with w (324) to free the pairs of segments, which are isolated (326), e.g. by gel electrophoresis. The isolated pairs are concatenated (328) in a conventional ligation reaction to produce concatemers of various sizes, which are separated, e.g. by gel electrophoresis. Concatemers greater than about 200-300 basepairs are isolated and cloned (330) into a standard sequencing vector, such as M13. The sequences of the cloned concatenated pairs are analyzed on a conventional DNA sequencer, such as a model 377 DNA sequencer from Perkin-Elmer Applied Biosystems Division (Foster City, Calif.).

In the above embodiment, the sequences of the pairs of segments are readily identified between sequences for the recognition site of the enzymes used in the digestions. For example, when pairs are concatenated from fragments of the r and s digestion after cleavage with a type IIs restriction endonuclease of reach (16/14), the following pattern is observed (SEQ ID NO: 1):

... NNNNrrrrrrNNNNNNNNNNNNNNNNNNNNqqqqqqNNNNN N ...

where "r" and "q" represent the nucleotides of the recognition sites of restriction endonuclease r and q, respectively, and where the N's are the nucleotides of the pairs of segments. Thus, the pairs are recognized by their length and their spacing between known recognition sites.

Pairs of segments are ordered by matching the sequences of segments between pairs. That is, a candidate map is built by selecting pairs that have one identical and one different sequence. The identical sequences are matched to form a candidate map, or ordering, as illustrated below for pairs ($s_1$, $s_2$), ($s_3$, $s_2$), ($s_3$, $s_4$), ($s_5$, $s_4$), and ($s_5$, $s_6$), where the "$s_k$'s" represent the nucleotide sequences of the segments:

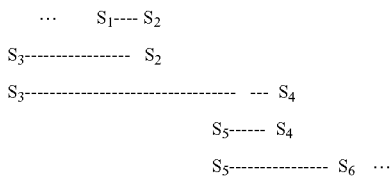

Sequence matching and candidate map construction is readily carried out by computer algorithms, such as the Fortran code provided in Appendix A. Preferably, a map construction algorithm initially sorts the pairs to remove identical pairs prior to map construction. That is, preferably only one pair of each kind is used in the reconstruction. If for two pairs, $(s_i, s_j)$ and $(s_m, s_n)$, $s_i=s_m$ and $s_j=s_n$, then one of the two can be eliminated prior to map construction. As pointed out above, such additional pairs either correspond to restriction fragments such as (92) of FIG. 1 (no sites of a second or third restriction endonuclease in its interior) or they are additional copies of pairs (because of sampling) that can be used in the analysis. Preferably, an algorithm selects the largest candidate map as a solution, i.e. the candidate map that uses the maximal number of pairs.

The vector of FIG. 2 can also be used for determining the frequency of expression of particular cDNAs in a cDNA library. Preferably, cDNAs whose frequencies are to be determined are cloned into a vector by way of flanking restriction sites that correspond to those of (206) and (210). Thus, cDNAs may be cleaved from the library vectors and directionally inserted into the vector of FIG. 2. After insertion, analysis is carried out as described for the mapping embodiment, except that a larger number of concatemers are sequenced in order to obtain a large enough sample of cDNAs for reliable data on frequencies.

EXAMPLE 1

Constructing a Physical Map of Yeast Chromosome I with Hind III, Eco RI, and Xba I In this example, a physical map of the 230 kilobase yeast chromosome 1 is constructed using pUC19 plasmids modified in accordance with FIG. 2. The chromosome is separately digested to completion with the following combinations of enzymes: Hind III and Eco RI, Hind III and Xba I, and Eco RI and Xba I to generate three populations of restriction fragments. Fragments from each population are inserted into separate pUC19 plasmids, one for each restriction fragment having different ends. That is, restriction fragments from the Hind III-Eco RI digestion are present in three types, ones with a Hind III-digested end and an Eco RI-digested end ("H-E" fragments), one with only Hind III-digested ends ("H-H" fragments), and ones with only Eco RI-digested fragments ("E-E" fragments). Likewise, restriction fragments from the Hind III-Kba I digestion are present in three types, ones with a Hind III-digested end and an Xba I-digested end ("H-X" fragments), one with only Hind III-digested ends ("H-H" fragments), and ones with only Xba I-digested fragments ("X-X" fragments). Finally, restriction fragments from the Xba I-Eco RI digestion are present in three types, ones with a Xba I-digested end and an Eco RI-digested end ("X-E" fragments), one with only Xba I-digested ends ("X-X" fragments), and ones with only Eco RI-digested fragments ("E-E" fragments). Thus, the plasmid for the Hind III-Eco RI digestion accepts H-E fragments; the plasmid for the Hind III-Xba I digestion accepts H-X fragments; and the plasmid for the Xba I-Eco RI digestion accepts X-E fragments. The construction of the plasmid for accepting H-E fragments is described below. The other plasmids are constructed in a similar manner. Synthetic oligonucleotides (i) through (iv) are combined with a Eco RI- and Hind III-digested pUC19 in a ligation reaction so that they assemble into the double stranded insert of Formula 1.

(i) 5'-AATTAGCCGTACCTGCAGCAGTGCAGAAGCTTGCGT (SEQ ID NO: 2)

(ii) 5'-AAACCTCAGAATTCCTGCACAGCTGCGAATCATTCG (SEQ ID NO: 3)

(iii) 5'-AGCTCGAATGATTCGCAGCTGTGCAGGAATTCTGAG (SEQ ID NO: 4)

(iv) 5'-GTTTACGCAAGCTTCTGCACTGCTGCAGGTACGGCT (SEQ ID NO: 5)

(SEQ ID NO: 6—top strand;
SEQ ID NO: 7—bottom strand)

Note that the insert has compatible ends to the Eco RI-Hind III-digested plasmid, but that the original Eco RI and Hind III sites are destroyed upon ligation. The horizontal arrows above and below the Bsg I and Bbv I sites indicate the direction of the cleavage site relative to the recognition site of the enzymes. After ligation, transformation of a suitable host, and expansion, the modified pUC19 is isolated and the insert is sequenced to confirm its identity.

Yeast chromosome I DNA is separated into three aliquots of about 5 µg DNA (0.033 pmol) each, which are then separately digested to completion with Hind III and Eco RI, Hind III and Xba 1, and Eco RI and Xba I, respectively. For each of the three populations, the same procedure is followed, which is described as follows for the pUC19 designed for H-E fragments.

Since each enzyme recognizes a six basepair recognition sequence, about 100-140 fragments are produced for a total of about 3.3 pmol of fragments, about fifty percent of which are H-E fragments. 5.26 µg (3 pmol) of plasmid DNA is digested with Eco RI and Hind III in Eco RI buffer as recommended by the manufacturer (New England Biolabs, Beverly, Mass.), purified by phenol extraction and ethanol precipitation, and ligated to the H-E fragments of the mixture in a standard ligation reaction. A bacterial host is transformed, e.g. by electroporation, and plated so that hosts containing recombinant plasmids are identified by white colonies. The digestion of the yeast chromosome I generates about 124 fragments of the three types, about fifty percent of which are H-E fragments and about twenty-five percent each are H-H or E-E fragments. About 290 colonies are picked for H-E fragments, and about 145 each are picked for H-H and E-E fragments. The same procedure is carried out for all the other types of fragments, so that six populations of transformed hosts are obtained, one each for H-E, H-X, X-E, H-H, E-E, and X-X fragments. Each of the populations is treated separately as follows: About 10 µg of plasmid DNA is digested to completion with Bsg I using the manufacturer's protocol (New England Biolabs, Beverly, Mass.) and after phenol extraction the vector/segment-containing fragment is isolated, e.g. by gel electrophoresis. The ends of the isolated fragment are then blunted by Mung bean nuclease (using the manufacturer's recommended protocol, New England Biolabs), after which the blunted fragments are purified by phenol extraction and ethanol precipitation. The fragments are then resuspended in a ligation buffer at a concentration of about 0.05 µg/ml in 20 1-ml reaction volumes. The dilution is designed to promote self-ligation of the fragments, following the protocol of Collins et al, Proc. Natl. Acad. Sci., 81: 6812-6816 (1984). After ligation and concentration by ethanol precipitation, phages from the 20 reactions are combined. The pairs of segments carried by the plasmids are then amplified by PCR using primers $p_1$ and $p_2$. The amplified product is purified by phenol extraction and ethanol precipitation, after which it is cleaved with Bbv I using the manufacturer's recommended protocol (New England Biolabs). After isolation by polyacrylamide gel electrophoresis, the pairs are concatenated by carrying out a conventional ligation reaction. The concatenated fragments are then separated by polyacrylamide gel electrophoresis and concatemers greater than about 200 basepairs are isolated and ligated into an equimolar mixture of three Phagescript SK sequencing vectors (Stratagene Cloning Systems, La Jolla, Calif.), separately digested with Hind III, Eco RI, and Hind III and Eco RI, respectively. (Other appropriate mixtures and digestions are employed when different combinations of enzymes are used). Preferably, a number of clones are expanded and sequenced that ensure with a probability of at least 99% that all of the pairs of the aliquot are sequenced. A "lane" of sequence data (about 600 bases) obtained with conventional sequencing provides the sequences of about 25 pairs of segments. Thus, after transfection, about 13 individual clones are expanded and sequenced on a commercially available DNA sequencer, e.g. PE Applied Biosystems model 377, to give the identities of about 325 pairs of segments. The other sets of fragments require an additional 26 lanes of sequencing (13 each for the H-X and X-E fragments).

Figure 4:
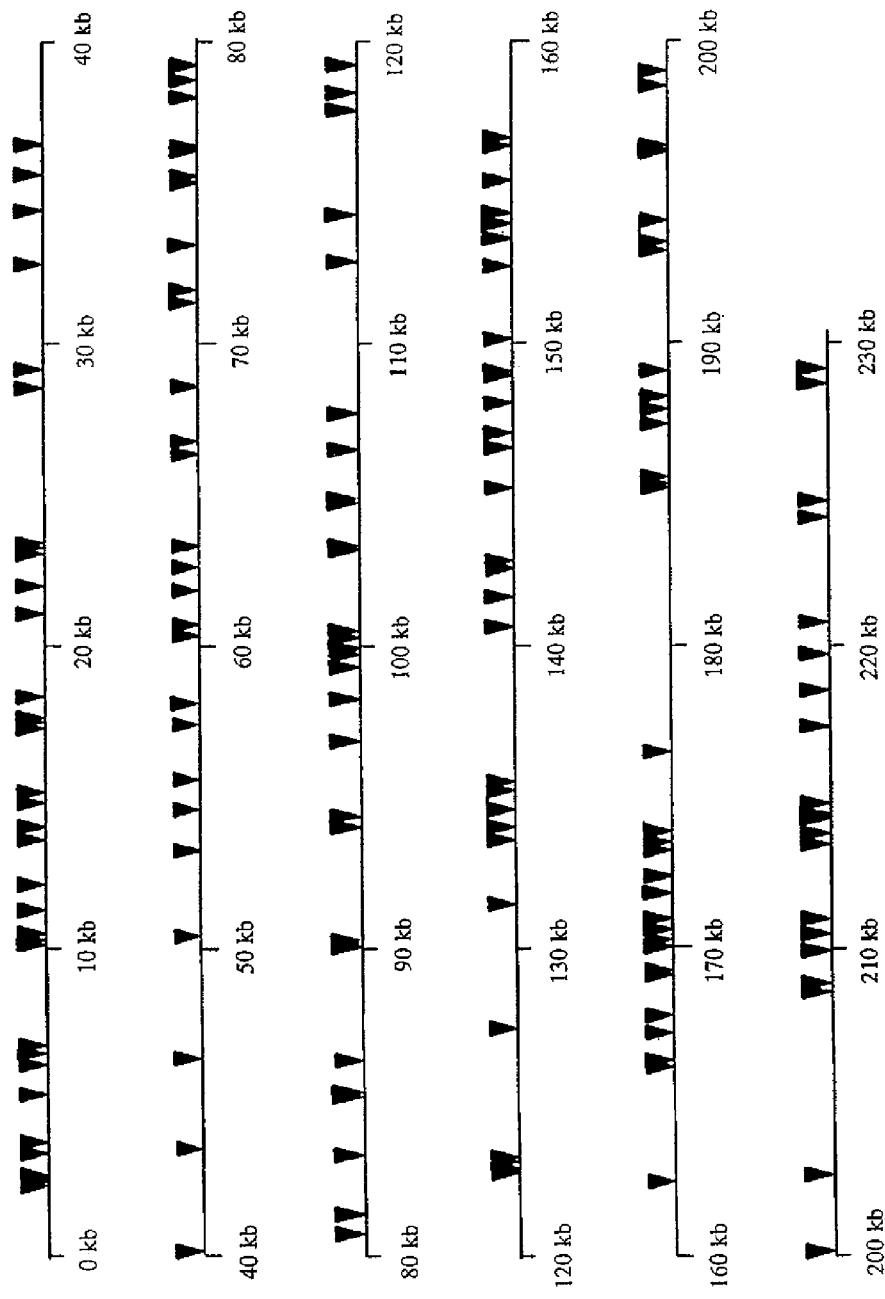
FIG. 4 illustrates locations on yeast chromosome 1 where sequence information is provided in a physical map based on digestions with Hind III, Eco RI, and Xba I in accordance with the invention.

FIG. 4 illustrates the positions on yeast chromosome 1 of pairs of segments ordered in accordance with the algorithm of Appendix A. The relative spacing of the segments along the chromosome is only provided to show the distribution of sequence information along the chromosome.

EXAMPLE 2

Directed Sequencing of Yeast Chromosome 1 Using Restriction Map Sequences as Spaced PCR Primers In this example, the 14-mer segments making up the physical map of Example 1 are used to separately amplify by PCR fragments that collectively cover yeast 1 chromosome. The PCR products are inserted into standard M13mp19, or like, sequencing vectors and sequenced in both the forward and reverse directions using conventional protocols. For fragments greater than about 800 basepairs, the sequence information obtained in the first round of sequencing is used to synthesized new sets of primers for the next round of sequencing. Such directed sequencing continues until each fragment is completely sequenced. Based on the map of Example 1, 174 primers are synthesized for 173 PCRs. The total number of sequencing reactions required to cover yeast chromosome 1 depends on the distribution of fragment sizes, and particularly, how many rounds of sequencing are required to cover each fragment: the larger the fragment, the more rounds of sequencing that are required for full coverage. Full coverage of a fragment is obtained when inspection of the sequence information shows that complementary sequences are being identified. Below, it is assumed that conventional sequencing will produce about 400 bases at each end of a fragment in each round. Inspection shows that the distribution of fragment sizes from the Example 1 map of yeast chromosome I are shown below together with reaction and primer requirements:

| Round of Sequencing | Fragment Size Range | No. of Fragments | No. of Seq. or PCR Primers | No. of Sequencing Reactions |
|---|---|---|---|---|
| 1 | >0 | 174 | 174 | 348 |
| 2 | >800 | 92 | 184 | 184 |
| 3 | >1600 | 53 | 106 | 106 |
| 4 | >2400 | 28 | 56 | 56 |
| 5 | >3200 | 16 | 32 | 32 |
| 6 | >4000 | 7 | 14 | 14 |
| 7 | >4800 | 5 | 10 | 10 |
| 8 | >5600 | 1 | 2 | 2 |
| | | Total No. of Primers | 578 | 752 |
| | | Seq. reactions for map: | | 39 |
| | | Total No. of Reactions: | | 791 |

This compares to about 2500-3000 sequencing reactions that are required for full coverage using shotgun sequencing.

APPENDIX A

| Computer Code for Ordering Pairs into a Physical Map |
|---|

```
c       program opsort
c
c       opsort reads ordered pairs from disk files
c       p1.dat, p2.dat, and p3.dat. and sorts
c       them into a physical map.
c
        character*1 op(1000,2,14),w(14),x(14)
        character*1 fp(1000,2,14),test(14)
c
c
        open(1,file='p1.dat',status='old')
        open(5,file='olist.dat',status='replace')
c
c
        nop=0
        read(1,100)nop1
        nop=nop + nop1
        do 101 j=1,nop
            read(1,102) (w(i),i=1,14),
     +                  (x(k),k=1,14)
        do 121 kk=1,14
            op(j,1,kk)=w(kk)
            op(j,2,kk)=x(kk)
```

APPENDIX A-continued

Computer Code for Ordering Pairs into a Physical Map

```
121         continue
101         continue
            read(1,100)nop2
            nop=nop + nop2
            do 1011 j=nop1+1,nop
              read(1,102) (w(i),i=1,14),
      +                   (x(k),k=1,14)
              do 1211 kk=1,14
                op(j,1,kk)=w(kk)
                op(j,2,kk)=x(kk)
1211          continue
1011        continue
c
            close(1)
c
            write(5,110)nop1,nop2,nop
110         format(3(2x,i4))
c
c
            open(1,file='p2.dat',status='old')
            read(1,100)nop3
            nop=nop + nop3
            do 104 j=nop1+nop2+1,nop
              read(1,102) (w(i),i=1,14),
      +                   (x(k),k=1,14)
              do 122 kk=1,14
                op(j,1,kk)=w(kk)
                op(j,2,kk)=x(kk)
122           continue
104         continue
c
            read(1,100)nop4
            nop=nop + nop4
            do 1041 j=nop1+nop2+nop3+1,nop
              read(1,102) (w(i),i=1,14),
      +                   (x(k),k=1,14)
              do 1221 kk=1,14
                op(j,1,kk)=w(kk)
                op(j,2,kk)=x(kk)
1221          continue
1041        continue
c
            close(1)
            write(5,1108)nop1,nop2,nop3,nop4,nop
1108        format(5(2x,i4))
c
c
            open(1,file='p3.dat',status='old')
            read(1,100)nop5
            nop=nop + nop5
            do 105 j=nop1+nop2+nop3+nop4+1,nop
              read(1,102) (w(i),i=1,14),
      +                   (x(k),k=1,14)
              do 123 kk=1,14
                op(j,1,kk)=w(kk)
                op(j,2,kk)=x(kk)
123           continue
105         continue
c
            read(1,100)nop6
            nop=nop + nop6
            do 1051 j=nop1+nop2+nop3+nop4+nop5+1,nop
              read(1,102) (w(i),i=1,14),
      +                   (x(k),k=1,14)
              do 1231 kk=1,14
                op(j,1,kk)=w(kk)
                op(j,2,kk)=x(kk)
1231          continue
1051        continue
c
            close(1)
            write(5,1109)nop1,nop2,nop3,nop4,nop5,nop6,nop
1109        format(7(2x,i4))
c
c
100         format(i4)
102         format(2(2x,14a1))
111         format(/)
c
c
            write(5,111)
            do 120 m=1,nop
              write(5,102) (op(m,1,i),i=1,14),
      +                    (op(m,2,k),k=1,14)
              write(*,102) (op(m,1,i),i=1,14),
      +                    (op(m,2,k),k=1,14)
120         continue
c
c
            write(5,111)
            do 1100 i=1,14
              test(i)=op(1,2,i)
              fp(1,1,i)=op(1,1,i)
              fp(1,2,i)=op(1,2,i)
1100        continue
c
            nxx=nop
            ns=1
c
1000        continue
            ne=0
            do 2000 ix=2,nxx
              nt=0
              do 2100 jx=1,14
                if(test(jx).ne.op(ix,1,jx)) then
                  nt=nt+1
                endif
2100          continue
              if(nt.eq.0) then
                ns=ns+1
c
                ne=ne+1
                if(ne.gt.1) then
                  write(*,1003)
1003            format(1x,'ne is gt 1')
                endif
c
                do 2200 kx=1,14
                  fp(ns,1,kx)=op(ix,1,kx)
                  fp(ns,2,kx)=op(ix,2,kx)
                  test(kx)=op(ix,2,kx)
2200            continue
                mm=0
                do 2300 mx=1,nxx
                  if(mx.eq.ix) then
                    goto 2300
                  else
                    mm=mm+1
                    do 2400 ma=1,14
                      op(mm,1,ma)=op(mx,1,ma)
                      op(mm,2,ma)=op(mx,2,ma)
2400                continue
                  endif
2300            continue
              endif
2000        continue
            nxx=nxx-1
            if(ne.ne.0) then
              goto 1000
            endif
c
c
            do 1220 m=1,ns
              write(5,102) (fp(m,1,i),i=1,14),
      +                    (fp(m,2,k),k=1,14)
              write(*,102) (fp(m,1,i),i=1,14),
      +                    (fp(m,2,k),k=1,14)
1220        continue
            write(*,100)ns
c
            close(5)
c
            end
```

I claim:

1. A method of polynucleotide sequencing, comprising:
   (a) providing a plurality of populations of target polynucleotide fragments, each of the target polynucleotide fragments having an internal nucleotide sequence and two ends, each of the target polynucleotide fragments being inserted into a circular vector;
   (b) cleaving the internal nucleotide sequence of each of the target polynucleotide fragments thereby removing the internal nucleotide sequence of each of the target polynucleotide fragments and leaving a segment of each end of the target polynucleotide fragments in the vector; and
   (c) determining the nucleotide sequences of the segment of each end of the target polynucleotide fragments in the vector after the cleaving step.

2. The method of claim 1, wherein the target polynucleotide fragments comprise genomic DNA sequences.

3. The method of claim 1, wherein the target polynucleotide fragments are fragments resulting from a restriction endonuclease digest of a target polynucleotide.

4. The method of claim 1, wherein step (b) further comprises circularizing the vector after said cleaving the internal nucleotide sequence of each of the target polynucleotide fragments.

5. The method of claim 1, further comprising amplifying a segment from an end of the target polynucleotide fragments by polymerase chain reaction after the cleaving step.

6. The method of claim 1, wherein the populations of target polynucleotide fragments are different.

7. The method of claim 1, wherein the target polynucleotide fragments are different.

8. The method of claim 1, wherein the circular vector comprises a first restriction endonuclease recognition site for a first restriction endonuclease flanking a 5' end of the target polynucleotide fragments, and a second restriction endonuclease recognition site for a second restriction endonuclease flanking a 3' end of the target polynucleotide fragments, and the cleavage sites of the first and second restriction endonucleases are within the internal nucleotide sequence of the target polynucleotide fragments, wherein the first and second restriction endonucleases are Type IIs restriction endonucleases.

9. The method of claim 8, wherein the first and second restriction endonuclease recognition sites are arranged such that the first restriction endonuclease recognizing said first restriction endonuclease recognition site cleaves the target polynucleotide fragments with a reach of 8/12 between its restriction endonuclease recognition site and its cleavage site, and the second restriction endonuclease recognizing said second restriction endonuclease recognition site cleaves the target polynucleotide fragments with a reach of 8/12 between its recognition site and its cleavage site.

10. The method of claim 8, wherein step (b) is performed with said first restriction endonuclease and said second restriction endonuclease, thereby producing restriction fragments comprising segments from the ends of the target polynucleotide fragments.

11. The method of claim 8, wherein the first and second restriction endonuclease recognition sites are arranged such that the first restriction endonuclease recognizing said first restriction endonuclease recognition site cleaves the target polynucleotide fragments with a reach of 12/13 between its restriction endonuclease recognition site and its cleavage site, and the second restriction endonuclease recognizing said second restriction endonuclease recognition site cleaves the target polynucleotide fragments with a reach of 12/13 reach between its recognition site and its cleavage site.

12. The method of claim 8, wherein the first and second restriction endonuclease recognition sites are arranged such that the first restriction endonuclease recognizing said first restriction endonuclease recognition site cleaves the target polynucleotide fragments with a reach of 16/14 between its restriction endonuclease recognition site and its cleavage site, and the second restriction endonuclease recognizing said second restriction endonuclease recognition site cleaves the target polynucleotide fragments with a reach of 16/14 reach between its recognition site and its cleavage site.

13. The method of claim 8, wherein the first and second restriction endonuclease recognition sites are arranged such that the first restriction endonuclease recognizing said first restriction endonuclease recognition site cleaves the target polynucleotide fragments with a reach of 20/18 between its restriction endonuclease recognition site and its cleavage site, and the second restriction endonuclease recognizing said second restriction endonuclease recognition site cleaves the target polynucleotide fragments with a reach of 20/18 between its recognition site and its cleavage site.

14. The method of claim 1, wherein step (c) comprises determining a nine base sequence located on the end of a segment from an end of the target polynucleotide fragments.

15. The method of claim 1, further comprising determining an ordering of the segments from the ends of the target polynucleotide fragments.

16. The method of claim 1, wherein said determining the nucleotide sequences of the segments of each end of the target polynucleotide fragments comprises performing a sequencing reaction on a DNA sequencer.

17. The method of claim 1, further comprising concatenating the segments from the ends of the target polynucleotide fragments prior to said determining the nucleotide sequences of the segments of each end of the target polynucleotide fragments in the vector.

* * * * *

UNITED STATES PATENT AND TRADEMARK OFFICE
CERTIFICATE OF CORRECTION

| | |
|---|---|
| PATENT NO. | : 8,975,024 B2 |
| APPLICATION NO. | : 14/044413 |
| DATED | : March 10, 2015 |
| INVENTOR(S) | : Stephen C. Macevicz |

Page 1 of 1

It is certified that error appears in the above-identified patent and that said Letters Patent is hereby corrected as shown below:

On the title page

In column 2 (page 2, item 56) at line 15, Under Other Publications, change ""FokI" to --"FokI--.

In column 2 (page 3, item 56) at line 1, Under Other Publications, change "21s" to --21st--.

In column 2 (page 3, item 56) at line 23, Under Other Publications, change "fot" to --for--.

In column 1 (page 4, item 56) at line 27, Under Other Publications, change "Biosytsems" to --Biosystems--.

In column 1 (page 4, item 56) at line 32, Under Other Publications, change "Biosytsems" to --Biosystems--.

In the specification

In column 2 at line 26, Change "invent" to --invention--.

In column 3 at line 51, Change "ihymidine," to --thymidine,--.

In column 3 at line 59, Change "oigonucleotide" to --oligonucleotide--.

In column 5 at lines 9-10, Change "polynucleoitde." to --polynucleotide.--.

In column 7 at line 58 (approx.), Change ".beta.-glactosidase" to --β-glactosidase--.

In columns 7-8 (Table 1) at line 3 (approx.), Change "gragments)" to --fragments)--.

In the claims

In column 18 at line 50, In Claim 11, change "12/13 reach" to --12/13--.

In column 18 at line 60, In Claim 12, change "16/14 reach" to --16/14--.

Signed and Sealed this
First Day of December, 2015

Michelle K. Lee
*Director of the United States Patent and Trademark Office*